US006376542B1

(12) United States Patent
Hansen et al.

(10) Patent No.: US 6,376,542 B1
(45) Date of Patent: *Apr. 23, 2002

(54) AQUEOUS MITICIDE COMPOSITIONS CONTAINING BENZYL BENZOATE

(75) Inventors: Eric J. Hansen, Ada; Jesse J. Williams, Hudsonville, both of MI (US)

(73) Assignee: Bissell Homecare, Inc., Grand Rapids, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/607,760

(22) Filed: Jun. 30, 2000

Related U.S. Application Data

(63) Continuation-in-part of application No. 09/184,456, filed on Nov. 2, 1998, now Pat. No. 6,107,341.
(60) Provisional application No. 60/068,270, filed on Dec. 19, 1997.

(51) Int. Cl.[7] .............................................. A01N 37/10
(52) U.S. Cl. ....................................... 514/544; 514/112
(58) Field of Search .................................. 514/544, 112

(56) References Cited

U.S. PATENT DOCUMENTS

| | | | |
|---|---|---|---|
| 3,808,319 A | | 4/1974 | Kanfoush |
| 3,996,379 A | | 12/1976 | Mihailovski |
| 4,666,940 A | * | 5/1987 | Bischoff et al. ............ 514/544 |
| 4,806,526 A | | 2/1989 | Green |
| 4,857,551 A | | 8/1989 | Tapolczay et al. |
| 4,877,811 A | | 10/1989 | Anthony et al. |
| 5,672,362 A | | 9/1997 | Burnett |
| 5,719,114 A | * | 2/1998 | Zocchi et al. ............... 510/383 |
| 5,839,155 A | | 11/1998 | Berglund et al. |
| 5,843,981 A | | 12/1998 | Miller |
| 5,854,288 A | | 12/1998 | Katsuda et al. |
| 5,905,066 A | * | 5/1999 | Zocchi et al. ............... 510/280 |
| 5,906,992 A | | 5/1999 | Fonsny et al. |
| 5,916,917 A | | 6/1999 | Suh et al. |
| 5,942,482 A | | 8/1999 | Zocchi et al. |
| 5,985,814 A | | 11/1999 | Zocchi et al. |
| 5,990,157 A | * | 11/1999 | Zocchi et al. ................ 514/464 |
| 6,107,341 A | * | 8/2000 | Hansen et al. .............. 514/544 |

FOREIGN PATENT DOCUMENTS

| | | | |
|---|---|---|---|
| EP | 566979 | * | 10/1993 |
| EP | 617612 | * | 9/1997 |
| GB | 1397475 | * | 6/1975 |
| JP | 60042314 | * | 3/1985 |
| JP | 601663804 | * | 8/1985 |
| JP | 61136600 | * | 6/1986 |
| RU | 2076707 | * | 4/1997 |
| SU | 567744 | * | 8/1977 |
| WO | 8912673 | * | 12/1989 |

* cited by examiner

*Primary Examiner*—Alton Pryor
(74) *Attorney, Agent, or Firm*—McGarry Bair LLP

(57) ABSTRACT

Compositions and methods for killing dust mites and cleaning carpets and other textile fabrics are disclosed. A miticide composition concentrate for mixing with water and optionally with a carpet or fabric cleaning solution consists essentially of a solution of benzyl benzoate and a water soluble organic solvent for the benzyl benzoate such as benzyl alcohol, a surfactant and water. The amounts of the solvent, surfactant and water are selected to maintain a stable dispersion of benzyl benzoate and benzyl alcohol in the aqueous mixture. Also disclosed are aqueous carpet cleaning miticide composition comprising benzyl benzoate, at least one organic solvent which has an affinity for benzyl benzoate and water, at least one surfactant, an anti-resoiling agent, optionally, a fragrance, optionally, a chelating agent and water. The amounts of the at least one organic solvent, surfactant and water are selected to solubilize the benzyl benzoate in the aqueous mixture and maintain a stable dispersion of benzyl benzoate and solvent in the aqueous mixture. Further, the at least one organic solvent and the at least one surfactant are selected to clean dirt and grease from a carpet surface or textile fabrics. The aqueous mixture is applied to surfaces of household furnishings including bedding, carpeting, and upholstery, using conventional liquid application techniques.

48 Claims, No Drawings

AQUEOUS MITICIDE COMPOSITIONS CONTAINING BENZYL BENZOATE

CROSS REFERENCE TO RELATED APPLICATIONS

This application is a continuation in part of U.S. patent application Ser. No. 09/184,456, filed Nov. 2, 1998, now U.S. Pat. No. 6,107,341 and claims the benefit of U.S. provisional patent application Ser. No. 60/068,270, filed Dec. 19, 1997.

FIELD OF THE INVENTION

This invention relates to methods and compositions for killing dust mites. In one of its aspects, the invention relates to a cleaning composition containing a miticide. In another of its aspects, the invention relates to a method for cleaning carpets. In another of its aspects, the invention relates to an aqueous concentrated miticide compositions.

BACKGROUND OF THE INVENTION

One of the most potent indoor allergens is house dust contaminated with dust mites. It is thought that dust mites may be an important factor in between 50 to 80 percent of all asthma cases, and contribute to countless cases of eczema, hay fever and other allergic reactions. Symptoms of hypersensitivity to dust mites include sneezing, itching, watery eyes, as well as headaches, fatigue and depression. Respiratory ailments associated with dust mites result from contact with proteins in the digestive juices from the dust mite gut which are carried on the fecal pellets, and exposure to dust mites in the first, critical year of life can trigger a lifelong allergy. There is no known cure for dust mite allergies, only prevention through the control of dust mite and related allergen levels, and de-sensitization injections.

Beds are the primary habitat for dust mites. A typical mattress may harbor anywhere from 100,000 to 10 million mites. Up to ten percent of a well-used pillow may be composed of dead mites and their droppings. Mites prefer warm, moist surroundings such as the top surfaces of a mattress while the human occupant is sleep, and their major source of food is the dead skin shed from humans and their pets. Significant numbers of mites can also be found in bedroom carpeting and household upholstery.

Currently, at least two products are commercially available for control of dust mites. They contain benzyl benzoate and/or tannic acid as active ingredients. Benzoic acid esters, such as benzyl benzoate, are effective agents for killing house dust mites based on laboratory testing and field evaluations. Benzyl benzoate does not pose a serious health risk when used in the amounts needed to kill mites because it is rapidly metabolized to hippuric acid, which is excreted in urine.

Although benzyl benzoate is an effective miticide, its use is not without problems. For cost and safety reasons, benzyl benzoate is diluted when used to control dust mites. However, benzyl benzoate is insoluble in water, and is therefore unstable as an aqueous spray. In commercial miticides, benzyl benzoate is adsorbed on solid particles to aid in its dispersion. The resulting dispersion is applied as either a moist powder or foam to carpets and bedding. One drawback is that the moist powder tends to clump together, so that it is difficult to apply evenly. Another drawback is that solid-stabilized benzyl benzoate miticides leave behind a powdery residue that is easily removed by vacuuming, which reduces its effectiveness.

The present invention is directed to overcoming, or at least minimizing, one or more of the problems set forth above.

SUMMARY OF THE INVENTION

According to the invention, a miticide composition concentrate for mixing with water and optionally with a carpet or fabric-cleaning solution consists essentially of a solution of benzyl benzoate and a solvent, a surfactant and water, wherein the amounts of solvent, surfactant and water are selected to maintain a stable dispersion of benzyl benzoate and solvent in the aqueous mixture. Preferably, the solvent includes benzyl alcohol and preferably is benzyl alcohol.

Preferably, the components are selected so that the concentrate solution is transparent.

The benzyl benzoate in the solution can vary over a fairly wide range but generally is in the range of 10 to 50 parts by weight, preferably in the range of 20 to 40 parts by weight and, in a preferred embodiment, 30 parts by weight. The concentration of the organic solvent in the mixture also varies over a fairly wide range, generally 10 to 50 parts by weight, preferably 15 to 35 parts by weight and, in a preferred embodiment of the invention, 22 parts by weight.

The surfactant in the concentrate can be any one of a number of surfactants, including a lipophillic surfactant, a hydrophobic surfactant, an anionic, a non-ionic, a cationic or an amphoteric surfactant, alone or in combination. The percentage of surfactant in the mixture can vary over a fairly wide range and generally is in the range of 1 to 20 weight parts per 100 weight parts of concentrate, preferably, in the range of 5 to 15 weight parts per 100 parts of concentrate and, in a preferred embodiment, is 10 weight parts per 100 weight parts of the concentrate. The balance in the concentrate is water.

The organic solvent in the concentrate can include aliphatic alcohols, aromatic alcohols and glycol ethers as well as benzyl alcohol. The preferred solvent is benzyl alcohol.

In the miticide concentrate, the ratio of benzyl benzoate to solvent is in the range of about 5:1 to about 1:5 by weight, preferably about 2:1.

Further according to the invention, a miticide/carpet-cleaning solution concentrate comprises by weight about 1 to 10 weight percent benzyl benzoate, about 1 to 10 weight percent of an organic solvent, preferably including benzyl alcohol, about 1 to 20 weight parts of a surfactant, about 1 to 6 parts of an anti-resoil agent, optionally a fragrance, and the balance being water. A chelating agent can also be incorporated into the concentrate.

The benzyl benzoate in the miticide/carpet-cleaning concentrate can vary over a relatively wide range of about 1 to 10 weight parts per 100 weight parts of concentrate. Preferably, the benzyl benzoate will be in the range of 3 to 7 weight parts and specifically 5 weight parts. The organic solvent performs the function of cleaning as well as solublizing the benzyl benzoate alcohol? in the aqueous solution. The organic solvent preferably includes benzyl benzoate, but can also include other solvents such as glycol ether, aliphatic alcohols and aromatic alcohols, alone or in combination.

A variety of surfactants can be used in the carpet-cleaning and miticide compositions. These surfactants include lipophillic surfactants, hydrophobic surfactants, anionic, non-ionic, cationic or amphoteric surfactants, alone or in combination can be used. The preferred surfactants are nonionic and anionic.

The surfactants can vary over a fairly wide range of about 1 to 20 parts of surfactant per 100 parts of concentrate solution. Preferably, the surfactants are in the range of 5 to 15 weight parts per 100 parts of concentrate. Preferred compositions include 9 to 12 weight parts of surfactant per 100 parts of solution.

The anti-resoil agent can vary over a fairly wide range of about 1 to 6 weight parts per 100 parts of concentrate. Preferably, the anti-resoil agent is in the range of 2 to 5 weight parts and preferably about 3 weight parts. Anti-resoil agents are well known and typically includes polymerized styrene/maleic anhydride.

The miticide/carpet-cleaning solution concentrate according to the invention is mixed with water in a ratio of 1 to 10 ounces of concentrate per gallon of water. The diluted composition is sprayed onto a carpet and then vacuumed up from the carpet, preferably after agitating the material into the carpet and/or allowing the material to reside in the carpet for a given length of time. The amount of concentrate can vary from 1 to 20 ounces per gallon of water, preferably in the range of 5 to 15 ounces of concentrate per gallon of water and preferably about 10 ounces of concentrate per gallon of water.

Thus, according to another aspect of the invention, a miticide/carpet-cleaning solution concentrate is diluted with water, preferably in the range of 1 to 20 ounces per gallon of water and sprayed onto a carpet or fabric surface. The solution is then vacuumed up from the carpet or fabric surface. Alternatively, the fabric can be rinsed with clear water and then dried.

In the miticide concentrate solution, water is present in an amount of at least 25% by weight. In the miticide/cleaning solution, water is present in an amount of at least 40% by weight.

An important aspect of the invention is that the miticide is a fully aqueous solution that, unlike heretofore available miticides, contains no solid particles for dispersing the benzyl benzoate. As a result, the solutions according to the invention do not leave behind particulate residue following application and are easy to apply with conventional deep cleaning equipment. In order to kill dust mites, existing miticide compositions rely on dust mites ingesting the solid carrier particles. Because these particles are easily removed by vacuuming, miticidal activity decreases sharply after the carpet is cleaned. In contrast, residual miticidal activity in the present invention is not significantly affected by vacuuming since the active ingredients in the miticide are adsorbed on the carpet fibers. Furthermore, since the aqueous mixture can be packaged as a liquid concentrate, it is easier to store, handle and apply than miticide adsorbed on bulky solid particles.

The miticide composition according the invention is advantageously combined with carpet and upholstery cleaning solutions and deposited onto carpet and upholstery surfaces with a conventional extraction cleaning machines. Suitable extraction cleaning machines are disclose in the U.S. patents to Kasen et al., U.S. Pat. No. 5,896,617, issued Apr. 27, 1999 and the U.S. Patent Application to Kasper et al., Ser. No. 09/112,527, filed Jul. 8, 1998, the disclosure of both of which are incorporated herein by reference.

The conventional carpet and upholstery cleaning compositions typically contain anionic and/or nonionic surfactants, an anti-soiling agent such as polymerized styrene/maleic anhydride, a solvent such as glycol ether, and a fragrance to impart a pleasant scent. Suitable carpet cleaning compositions are disclosed in the Campagna et al. U.S. Pat. No. 5,955,413 and Scialla et al. U.S. Pat. No. 5,928,384, both of which are incorporated herein by reference. Examples of suitable cleaning solutions which can be used with the invention include: BISSELL Fiber Cleansing Formula, Hoover Steam Vac carpet/upholstery detergent, Dirt Devil carpet & rug shampoo, Rug Doctor Steam Cleaner, and Full Release Professional Carpet Cleaner by Oreck.

DESCRIPTION OF THE PREFERRED EMBODIMENTS

In one embodiment, the miticide composition according to the invention comprises an aqueous mixture of benzyl benzoate, a solvent and a surfactant. Because benzyl benzoate is insoluble in water, it is combined with sufficient solvent to maintain a stable dispersion of benzyl benzoate in the aqueous mixture. The aqueous mixture can then be applied to surfaces that may harbor dust mites—carpets, bedding, upholstery, and the like—using conventional techniques. Since the solvent obviates the need for a solid carrier, the disclosed miticide does not leave behind particulate residue following application.

The aqueous benzyl benzoate mixture can be an emulsion of a colloidal dispersion of benzyl benzoate in water and solvent. Or, it can be a true solution, in which the benzyl benzoate, solvent, and water are uniformly dispersed at the molecular level. In either case, once benzyl benzoate is uniformly dispersed in the aqueous mixture, the solvent helps maintain a stable dispersion by preventing benzyl benzoate from coalescing prior to application. Ideally, the aqueous miticide mixtures are transparent.

Suitable solvents show a high affinity for benzyl benzoate and for water and are therefore at least partially soluble in both. Examples of useful solvents include aliphatic alcohols, aromatic alcohols, glycol ethers, or combinations of aliphatic alcohols, aromatic alcohols and glycol ethers. Specific examples thus include ethyl alcohol, isopropyl alcohol, and benzyl alcohol. Benzyl alcohol is especially useful because, like benzyl benzoate, it is effective in killing dust mites.

In aqueous miticides comprising benzyl benzoate, benzyl alcohol, and water, the ratio of benzyl alcohol to benzyl benzoate is typically in a range of about 5:1 to about 1:5 by weight. Generally, the ratio depends on the total amount of benzyl benzoate and benzyl alcohol present in the aqueous mixture, and on the presence of any additional components, such as surfactants, deodorants, colorants, anti-allergenic compounds, and the like. Studies show that, in the absence of surfactants, a 2:1 weight ratio of benzyl alcohol to benzyl benzoate works well for most commercially viable, safe, and efficacious levels of benzyl alcohol and benzyl benzoate. For the purposes of this disclosure, a miticide is considered effective if it kills at least 80 percent of a given dust mite population following application.

Generally, aqueous miticide compositions comprising from about 0.01% to about 5% benzyl benzoate and benzyl alcohol solution by weight are effective in killing dust mites. Because the aqueous mixtures are effective over such a wide range of benzyl benzoate and benzyl alcohol concentrations, the aqueous miticides can be packaged as concentrates, which are diluted with water prior to application. Such concentrates will normally contain from about 1.0% to about 5% benzyl benzoate and benzyl alcohol solution. For example, research shows that a 2.5 wt. % aqueous mixture of a 2:1 weight ratio of benzyl alcohol to benzyl benzoate can kill about 95% of a dust mite population following application.

In addition to benzyl benzoate and solvent, the miticide composition also contains one or more surfactants. Surfactants help maintain a stable colloidal dispersion of benzyl benzoate in the aqueous mixture. By adding the proper amount of surfactant and solvent, the benzyl benzoate forms a stable, transparent aqueous emulsion. If packaged as a concentrate, the clear benzyl benzoate emulsion will usually turn cloudy or white when diluted with water.

Common surfactants can be anionic, non-ionic, cationic, lipophillic, hydrophobic, or amphoteric substances commonly used in textile cleansers. Examples of anionic surfactants include sulfonated aromatic and aliphatic hydrocarbons, sulfonated alpha-olefins, sulfated fatty alcohols and fatty alcohol ethers, sulfonated fatty acid methyl esters, sulfonated maleic acid esters, and carboxymethylated fatty alcohol polyglycol ethers. Examples of non-ionic surfactants include fatty alcohol ethoxylates, alkylphenol ethoxylates, fatty acid ethoxylates, fatty acid alkylolamides, fatty acid alkylolamide ethoxylates, fatty amine ethoxylates, and polyalkylene oxide block polymers. Cationic and amphoteric surfactants include quaternary ammonium compounds such as fatty amine carboxylates and betaines such as alkylampha-propinates and alkyl imidazolines, respectively.

The amount of surfactant in the aqueous mixture depends on the concentration of benzyl benzoate and solvent. Surfactants usually comprise from about 1% to about 20% of the concentrated aqueous mixture, but their relatively high cost, their tendency to leave a solid residue and their possible toxicity all limit their use. A useful concentrated aqueous miticide containing benzyl benzoate and benzyl alcohol contains about 10–12 wt. % of a surfactant. Studies show that less solvent is needed if a surfactant is used. For example, an aqueous miticide having a 1:1 weight ratio of benzyl alcohol to benzyl benzoate with a surfactant performs better than an aqueous miticide having a 2:1 weight ratio of benzyl alcohol to benzyl benzoate without a surfactant.

Since the disclosed miticide is an aqueous solution, it can be applied to carpets, bedding, upholstery and the like by any method suitable for applying liquids. One particularly advantageous method is to apply the miticide with a conventional deep cleaner or extraction cleaner with or without a conventional cleaning composition. The deep cleaner evenly applies the aqueous miticide by spraying the aqueous mixture on carpeted areas so that the miticide can penetrate deep within the carpet pile. Preferably, the aqueous miticide is combined with a conventional cleaning solution to dissolve dirt and other contaminants, and dislodge materials that may either foster the growth of dust mites, such as human skin particles and animal dander, or cause an allergic reaction—dust mite fecal pellets and carcasses, for example. Conventional carpet cleaning compositions are commercially available from a variety of sources, including BISSELL Inc., and other manufacturers of deep cleaning or extraction cleaning machines as well as others. These carpet cleaning compositions typically contain a variety of ingredients adapted to remove dirt and grease from carpets, to prevent resoiling of carpets after cleaning and fragrances. Typical ingredients include anionic and/or nonionic surfactants, an anti-soiling agent such as polymerized styrene/maleic anhydride and an organic solvent such as glycol ether. Many of these commercial carpet cleaning compositions are used for upholstery and other fabrics with the deep cleaning machines.

When using a commercial carpet or fabric cleaning composition, the relative amounts of miticide composition, cleaning composition and water can vary over a large range, depending on the conditions. The relative amounts of cleaning solution and water can vary over a wide range, dependent on the amount of soil in the carpet. However, the amount of miticide composition should be sufficient so that the range of benzyl benzoate in the composition at least 0.01% by weight and generally in the range of about 0.01 –about 1% by weight.

After the aqueous miticide is sprayed on the carpet, about 50–80% of the aqueous mixture is removed by vacuuming. Vacuuming also removes materials that may cause allergic reactions including dust mite fecal pellets and carcasses, dissolved dirt and other contaminants. Human skin particles and animal dander that are later ingested by dust mites readily absorb miticide that remains in the carpet after vacuuming. Thus, the aqueous miticide continues to kill dust mites long after the initial application. Unlike miticides adsorbed on solid carriers, the residual aqueous miticide is adsorbed on carpet fibers and is therefore available to taint dust mite food that finds its way onto the carpet after miticide application.

In addition to carpets, the aqueous miticide can be applied to other surfaces including draperies, bedding and upholstery using adapters that are typically provided with deep cleaners. Furthermore, the aqueous miticide can be applied to surfaces using conventional liquid spraying devices.

EXAMPLES

The follow examples are intended as illustrative and non-limiting, and represent specific embodiments of the present invention.

Example 1.

A miticide composition was prepared by mixing together the following ingredients by weight:

|  | Wt. Parts | wt. % |
|---|---|---|
| Benzyl Benzoate | 5.0 | 5.0 |
| Benzyl Alcohol- | 3.0 | 3.0 |
| LF/RA 30* | 2.0 | 2.0 |
| IL 2868** | 6.0 | 6.0 |
| Fragrance | 0.15 | 0.15 |

This mixture made a clear solution of benzyl benzoate in benzyl alcohol. To this mixture was added the following ingredients:

|  | Wt. Parts | wt. % |
|---|---|---|
| Water | 68.35 | 68.35 |
| DX6-178*** | 12.5 | 12.5 |
| LC-40B**** | 2.0 | 2.0 |
| UFL****** | 1.0 | 1.0 |
| TOTAL | 100 | 100 |

* A non-ionic surfactant manufactured by ICI Chemicals and Polymers Ltd.
** A non-ionic surfactant manufactured by Iniqema.
*** An anti-soiling agent manufactured by Interpolymer Corporation
**** A chellating agent manufactured by Callaway Chemical Co.
***** An aninoic surfactant manufactured by Rutgers Organics Corp.

The mixture formed a clear solution which was then further diluted with water in a commercial deep cleaning extractor. One part by weight of the above miticide cleaning solution were mixed with 25 weight parts of water in a BISSELL commercial carpet cleaning extractor and was sprayed onto 3 carpet samples and tested for % cleaning using a standard test procedure BDT-101/102. The carpet samples were then also tested for miticide kill using an actual count in a sample. The percent cleaning was 36.5% and the miticide kill rate was 85–100%. Example 2.

A miticide composition was prepared by mixing together the following ingredients by weight:

|  | Wt. Parts | wt. % |
|---|---|---|
| Benzyl Benzoate | 5.0 | 5.0 |
| Benzyl Alcohol | 3.0 | 3.0 |
| LF/RA 30* | 4.0 | 4.0 |
| IL 2868** | 4.0 | 4.0 |
| PNP Glycol ether | 2.0 | 2.0 |
| Fragrance | 0.15 | 0.15 |

This mixture made a clear solution of benzyl benzoate in benzyl alcohol and glycol ether. To this mixture was added the following ingredients:

|  | Wt. Parts | wt. % |
|---|---|---|
| Water | 63.35 | 63.35 |
| DX6-178*** | 12.5 | 12.5 |
| LC-40B**** | 2.0 | 2.0 |
| UFL****** | 4.0 | 4.0 |
| TOTAL | 100 | 100 |

\* A non-ionic surfactant manufactured by ICI Chemicals and Polymers Ltd.

\*\* A non-ionic surfactant manufactured by Iniqema.

\*\*\* An anti-soiling agent manufactured by Interpolymer Corporation

\*\*\*\* A chellating agent manufactured by Callaway Chemical Co.

\*\*\*\*\* An aninoic surfactant manufactured by Rutgers Organics Corp.

The mixture formed a clear solution which was then further diluted with water in a commercial deep cleaning extractor. One part by weight of the above miticide cleaning solution were mixed with 25 weight parts of water in a BISSELL commercial carpet cleaning extractor and was sprayed onto 3 carpet samples and tested for % cleaning using a standard test procedure BDT-101/102. The carpet samples were then also tested for miticide kill using an actual count in a sample. The percent cleaning was 35.6% and the miticide kill rate was 85–100%.

Example 3.

A control composition with the formulation of a BISSELL Carpet Care Allergen Control cleaning solution was prepared and diluted with water as in Example 1. The BISSELL Carpet Care Allergen Control formula had the following composition:

|  | Amount | CAS Number |
|---|---|---|
| Active Ingredients |  |  |
| Acrylate Copolymer | 2.4–2.6% | 25035-81-8/1314-13-2 |
| Dihexyl Sodium Sulfosuccinate | 1.8–2.0% | 3006-15-3 |
| Capryloamphopropionate | 1.4–1.6% | 68630-95-5 |
| Glycol Ether | 2.9–3.1% | 111-76-2 |
| Sodium Ethylenediaminetetraacetate | 1.5–1.7% | 64-02-8 |
| Inactive Ingredients |  |  |
| Water | 74.9–80.1% | 7732-18-5 |
| Silicone-glycol Emulsion | 0.009–0.011 | 25322694/63148629 |
| Fragrance | 0.14–0.16% | None-Trade Secret |

This diluted carpet cleaning solution mixture was sprayed onto 3 carpet samples and tested for cleaning efficiency using a standard test procedure BDT-101/102 and for miticide kill using an actual count in a sample. The cleaning efficiency was 35% and the miticide kill rate was 40–60%.

It is to be understood that the above description is intended to be illustrative and not restrictive. Reasonable variations and modifications are possible within the scope of the forgoing description of the invention and will be apparent to those of skill in the art to which the invention pertains without departing from the spirit of the invention. The scope of the invention should, therefore, be determined with reference to the appended claims, along with the full scope of equivalents to which such claims are entitled.

What is claimed is:

1. A miticide composition concentrate for mixing with water and optionally with a carpet or fabric cleaning solution and consisting essentially of:
   a solution of benzyl benzoate and benzyl alcohol;
   a surfactant; and
   water;
   wherein the amounts of the benzyl alcohols surfactant and water are selected to maintain a stable dispersion of benzyl benzoate and benzyl alcohol in the aqueous mixture.

2. The miticide composition concentrate of claim 1 wherein the concentrate solution is transparent.

3. The miticide composition concentrate of claim 1 wherein the solution of benzyl benzoate and benzyl alcohol in the miticide composition concentrate is in the range of about 1.0 to about 5.0% by weight.

4. The miticide composition concentrate of claim 1 wherein the surfactant is present in an amount from about 1 to about 20 weight % of the miticide composition concentrate.

5. The miticide composition concentrate of claim 1 wherein the benzyl benzoate is present in an amount from about 10 to about 50 weight % of the miticide composition concentrate.

6. The miticide composition concentrate of claim 5 wherein the benzyl alcohol is present in an amount from about 50 to about 10 weight % of the miticide composition concentrate.

7. The miticide composition concentrate of claim 5 wherein the benzyl benzoate is present in an amount from about 20 to about 40 weight % of the miticide composition concentrate.

8. The miticide composition concentrate of claim 7 wherein the benzyl alcohol is present in an amount from about 40 to about 20 weight % of the miticide composition concentrate.

9. The miticide composition concentrate of claim 8 wherein the surfactant is present in an amount from about 5 to about 15 weight % of the miticide composition concentrate.

10. The miticide composition concentrate of claim 7 wherein the benzyl benzoate is present in an amount of about 30 weight % of the miticide composition concentrate.

11. The miticide composition concentrate of claim 10 wherein the benzyl alcohol is present in an amount of about 22 weight % of the miticide composition concentrate.

12. The miticide composition concentrate of claim 11 wherein the surfactant is present in an amount of about 10 weight % of the miticide composition concentrate.

13. The miticide composition concentrate of claim 1 wherein the water is present in an amount of at least 25 weight % of the miticide composition concentrate.

14. A miticide composition concentrate for mixing with water and optionally with a carpet or fabric cleaning solution and consisting essentially of:
   a solution of benzyl benzoate and an organic solvent which has an affinity for benzyl benzoate and water;
   a surfactant; and
   water;
   wherein the amounts of the organic solvent, surfactant and water are selected to maintain a stable dispersion of benzyl benzoate and solvent in the aqueous mixture.

15. The miticide composition concentrate according to claim 14 wherein the organic solvent is selected from the group consisting of aliphatic alcohol, an aromatic alcohol, a glycol ether, and benzyl alcohol, alone or in combination.

16. The miticide composition concentrate according to claim 15 wherein the aliphatic alcohol includes isopropyl alcohol and ethyl alcohol, alone or in combination.

17. The miticide composition concentrate according to claim 14 wherein the surfactant is present in an amount from about 1 to about 20 weight % of the miticide composition concentrate; the benzyl benzoate is present in an amount from about 10 to about 50 weight % of the miticide composition concentrate; and organic solvent is present in an amount from about 50 to about 10 weight % of the miticide composition concentrate.

18. The miticide composition concentrate according to claim 17 wherein the water is present in an amount of at least 25 weight % of the miticide composition concentrate.

19. The miticide composition concentrate of claim 14 wherein the benzyl benzoate is present in an amount from about 20 to about 40 weight % of the miticide composition concentrate; the organic solvent is present in an amount from about 40 to about 20 weight % of the miticide composition concentrate; and the surfactant is present in an amount from about 5 to about 15 weight % of the miticide composition concentrate.

20. The miticide composition concentrate according to claim 19 wherein the water is present in an amount of at least 25 weight % of the miticide composition concentrate.

21. The miticide composition concentrate of claim 14 wherein the benzyl benzoate is present in an amount of about 30 weight % of the miticide composition concentrate; the organic solvent is present in an amount of about 22 weight % of the miticide composition concentrate; and the surfactant is present in an amount of about 10 weight % of the miticide composition concentrate.

22. The miticide composition concentrate according to claim 21 wherein the water is present in an amount of at least 25 weight % of the miticide composition concentrate.

23. An aqueous carpet cleaning miticide composition comprising:
   benzyl benzoate;
   at least one organic solvent selected from the group consisting of aliphatic alcohol, an aromatic alcohol, a glycol ether, and benzyl alcohol, alone or in combination and which has an affinity for benzyl benzoate and water;
   at least one surfactant; and
   water;
   an anti-resoiling agent;
   optionally, a fragrance;
   optionally, a chellating agent;
   wherein the amounts of the at least one organic solvents surfactant and water are selected to solubilize the benzyl benzoate in the aqueous mixture and maintain a stable dispersion of benzyl benzoate and solvent in the aqueous mixture and further wherein the at least one organic solvent and the at least one surfactant are selected to clean dirt and grease from a carpet surface or textile fabrics.

24. The aqueous carpet cleaning miticide composition of claim 23 wherein the surfactant is present in an amount from about 1 to about 20 weight % of the carpet cleaning miticide composition; the benzyl benzoate is present in an amount from about 1 to about 10 weight % of the carpet cleaning miticide composition; the anti-resoiling agent is present in an amount of about 1–6 weight %; and the at least one organic solvent is present in an amount from about 1 to about 10 weight % of the carpet cleaning miticide composition.

25. The aqueous carpet cleaning miticide composition of claim 24 wherein the water is present in an amount of at least 40 weight % of the miticide composition concentrate.

26. The aqueous carpet cleaning miticide composition of claim 23 wherein the benzyl benzoate is present in an amount from about 3 to about 7 weight % of the aqueous carpet cleaning miticide composition; the at least one organic solvent is present in an amount from about 2 to about 8 weight % of the aqueous carpet cleaning miticide composition; the anti-resoiling agent is present in an amount of about 2–5 weight %; and the surfactant is present in an amount from about 5 to about 15 weight % of the aqueous carpet cleaning miticide composition.

27. The aqueous carpet cleaning miticide composition of claim 26 wherein the water is present in an amount of at least 40 weight % of the aqueous carpet cleaning miticide composition.

28. The aqueous carpet cleaning miticide composition of claim 23 wherein the benzyl benzoate is present in an amount of about 5 weight % of the miticide composition concentrate; the organic solvent is present in an amount of about 3–5 weight % of the miticide composition concentrate; the surfactant is present in an amount of about 9–12 weight % of the miticide composition concentrate; and the anti-resoiling agent is present in an amount of about 3 weight % of the miticide composition concentrate.

29. The aqueous carpet cleaning miticide composition of claim 23 wherein the water is present in an amount of at least 40 weight % of the miticide composition concentrate.

30. The aqueous carpet cleaning miticide composition of claim 23 wherein the surfactant is a lipophillic surfactant, a hydrophobic surfactant, an anionic, a non-ionic, a cationic or an amphoteric surfactant, alone or in combination.

31. A method for cleaning a carpet or fabric surface and at the same time killing dust mites comprising the steps of:
   admixing the aqueous carpet cleaning miticide composition of claim 23 with water;

applying the aqueous carpet cleaning miticide composition and water mixture to a carpet or fabric surface to dissolve or suspend soil in the carpet or fabric in the fabric cleaning/ miticide mixture and at the same time killing dust mites in the carpet or fabric; and extracting a soiled aqueous solution from the carpet or fabric to remove soil from the carpet and leaving a miticide compound in the carpet or fabric.

32. A method for cleaning a carpet or fabric surface according to claim 31 wherein from 1–20 oz. of the aqueous carpet cleaning miticide composition are mixed with a gallon of water in the admixing step.

33. A method for cleaning a carpet or fabric surface according to claim 31 wherein from 5–15 oz. of the aqueous carpet cleaning miticide composition are mixed with a gallon of water in the admixing step.

34. A method for cleaning a carpet or fabric surface according to claim 31 wherein about 10 oz. of the aqueous carpet cleaning miticide composition are mixed with a gallon of water in the admixing step.

35. A method for cleaning a carpet or fabric surface according to claim 31 wherein the at least one organic solvent includes benzyl alcohol.

36. A method for cleaning a carpet or fabric surface according to claim 31 wherein the at least one organic solvent is selected from the group consisting of aliphatic alcohol, an aromatic alcohol, a glycol ether, and benzyl alcohol, alone or in combination.

37. A method for cleaning a carpet or fabric surface according to claim 31 wherein the surfactant is present in an amount from about 1 to about 20 weight % of the carpet cleaning miticide composition; the benzyl benzoate is present in an amount from about 1 to about 10 weight % of the carpet cleaning miticide composition; the anit-resoiling agent is present in an amount of about 1–6 weight %; and the at least one organic solvent is present in an amount from about 1 to about 10 weight % of the carpet cleaning miticide composition.

38. A method for cleaning a carpet or fabric surface according to claim 37 wherein the water is present in an amount of at least 40 weight % of the carpet cleaning miticide composition.

39. A method for cleaning a carpet or fabric surface according to claim 31 wherein the benzyl benzoate is present in an amount from about 3 to about 7 weight % of the aqueous carpet cleaning miticide composition; the at least one organic solvent is present in an amount from about 2 to about 8 weight % of the aqueous carpet cleaning miticide composition; the anti-resoiling agent is present in an amount of about 2–5 weight %; and the surfactant is present in an amount from about 5 to about 15 weight % of the aqueous carpet cleaning miticide composition.

40. A method for cleaning a carpet or fabric surface according to claim 39 wherein the water is present in an amount of at least 40 weight % of the aqueous carpet cleaning miticide composition.

41. A method for cleaning a carpet or fabric surface according to claim 31 wherein the benzyl benzoate is present in an amount of about 5 weight % of the miticide composition concentrate; the organic solvent is present in an amount of about 3–5 weight % of the miticide composition concentrate; the surfactant is present in an amount of about 9–12 weight % of the miticide composition concentrate; and the anti-resoiling agent is present in an amount of about 3 weight % of the miticide composition concentrate.

42. A method for cleaning a carpet or fabric surface according to claim 41 wherein the water is present in an amount of at least 40 weight % of the miticide composition concentrate.

43. A method for cleaning a carpet or fabric surface according to claim 31 wherein the surfactant is a lipophillic surfactant, a hydrophobic surfactant, an anionic, a non-ionic, a cationic or an amphoteric surfactant, alone or in combination.

44. A method for cleaning a carpet or fabric surface according to claim 31 wherein the surface is a carpet surface.

45. A method for cleaning a carpet or fabric surface according to claim 31 wherein the surface is a bedding surface.

46. A method for cleaning a carpet or fabric surface according to claim 31 wherein the surface is an upholstered surface.

47. The aqueous carpet cleaning miticide composition of claim 23 wherein the anti-soiling agent is polymerized styrene/maleic anhydride.

48. The aqueous carpet cleaning miticide composition of claim 23 wherein the at least one organic solvent includes benzyl alcohol.

* * * * *

UNITED STATES PATENT AND TRADEMARK OFFICE
CERTIFICATE OF CORRECTION

PATENT NO.     : 6,376,542 B1
DATED          : April 23, 2002
INVENTOR(S)    : Eric J. Hansen and Jesse J. Williams It is certified that error appears in the above-identified patent and that said Letters Patent is hereby corrected as shown below:

<u>Column 8,</u>
Line 38, "alcohols" should be -- alcohol, --.

<u>Column 10,</u>
Line 12, "solvents" should be -- solvent, --.

Signed and Sealed this

Third Day of September, 2002

Attest:

Attesting Officer

JAMES E. ROGAN
Director of the United States Patent and Trademark Office